United States Patent [19]

Hirata et al.

[11] Patent Number: 4,694,001
[45] Date of Patent: Sep. 15, 1987

[54] β-LACTAM COMPOUND AND A PHARMACEUTICAL COMPOSITION CONTAINING THE SAME

[75] Inventors: Tadashi Hirata, Yokohama; Kenichi Mochida, Hiratsuka; Chihiro Shiraki, Machida; Kiyoshi Sato, Mishima, all of Japan

[73] Assignee: Kyowa Hakko Kogyo Co., Ltd., Tokyo, Japan

[21] Appl. No.: 674,710

[22] Filed: Nov. 26, 1984

Related U.S. Application Data

[63] Continuation of Ser. No. 591,254, Mar. 20, 1984, abandoned, which is a continuation of Ser. No. 424,633, Sep. 27, 1982, abandoned.

[30] Foreign Application Priority Data

Oct. 1, 1981 [JP] Japan ................... 56-156752

[51] Int. Cl.$^4$ ................... C07D 205/12; A61K 31/395
[52] U.S. Cl. ................... 514/210; 540/205; 540/222; 540/227
[58] Field of Search ................... 544/25, 26, 27; 514/210; 540/205

[56] References Cited

U.S. PATENT DOCUMENTS

| | | | |
|---|---|---|---|
| 4,252,952 | 2/1981 | Takano et al. | 544/22 |
| 4,275,062 | 6/1981 | Breuer et al. | 544/22 |
| 4,291,164 | 9/1981 | Hirata et al. | 540/205 |
| 4,343,943 | 8/1982 | Hirata et al. | 540/205 |

FOREIGN PATENT DOCUMENTS

| | | |
|---|---|---|
| 2353557 | 12/1977 | France . |
| 2362856 | 3/1978 | France . |
| 2429220 | 1/1980 | France . |
| 2025971 | 1/1980 | United Kingdom . |

Primary Examiner—Nicholas S. Rizzo
Attorney, Agent, or Firm—Fitzpatrick, Cella, Harper & Scinto

[57] ABSTRACT

β-Lactam compounds represented by the general formula:

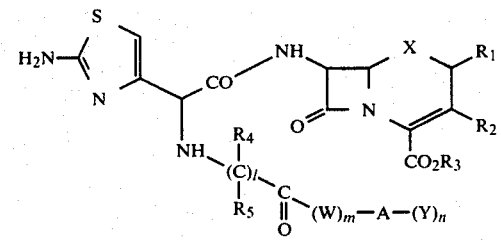

(wherein X represents $CH_2$, S or O; Y represents a hydroxyl group, a lower alkanoyloxy group or a lower alkoxycarbonyloxy group; W is a group represented by $CH_2$, NH,

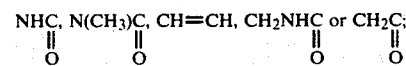

A is a phenyl group, a naphthyl group, or a monocyclic or dicyclic heterocyclic group, respectively substituted by $(Y)_n$; $R_4$ and $R_5$ each are a hydrogen atom, a lower alkyl group, or a cycloalkylidene group with a carbon atom combined therewith; l is 0 or an integer of 1, 2 or 3; m is 0 or 1; n is an integer of 1, 2, 3, 4 or 5; and $R_1$, $R_2$ and $R_3$ are groups often used in the conventional β-lactam compounds) have strong antimicrobial activities against a wide range of Gram positive and negative bacteria; particularly Gram negative bacteria including *Pseudomonas aeruginosa*, *Pseudomonas sepatia* and various *Enterobacters*.

5 Claims, No Drawings

β-LACTAM COMPOUND AND A PHARMACEUTICAL COMPOSITION CONTAINING THE SAME

This application is a continuation of application Ser. No. 591,254, filed Mar. 20, 1984, now abandoned, which is a continuation of application Ser. No. 424,633, filed Sept. 27, 1982, now abondoned.

BACKGROUND OF THE INVENTION

The present invention relates to a β-lactam compound wherein a specific acyl group, etc., are substituted for a hydrogen atom of the amino group of the 2-aminoacetamido group of a cephalosporin or an analog thereof (containing carbacephem nucleus) having a 7-[2-(2-aminothiazol-4-yl)-2-amino]acetamido group, a related compound thereof, and a pharmaceutical composition containing said β-lactam compound.

Many β-lactam antibotics have been developed in order to provide good chemical medicaments for curing various microbial infections. Among these compounds, β-lactam compounds wherein a hydrogen atom of the amino group of the 2-aminoacetamido group of a cephalosporin or an analog thereof having a 7-[2-(2-amino-thiazol-4-yl)-2-amino]acetamido group is substituted by various groups have been known [J. Antibiotics 35, 1022 (1980), U.S. Pat. No. 4,311,842, etc.].

It has been found that the β-lactam compounds of the present invention have strong antimicrobial activities against a wide range of Gram positive and negative bacteria, particularly Gram negative bacteria including *Pseudomonas aeruginosa, Pseudomonas sepatia* and various Enterobacters.

DETAILED DESCRIPTION OF THE INVENTION

This invention relates to (1) a novel β-lactam compound represented by the general formula (I):

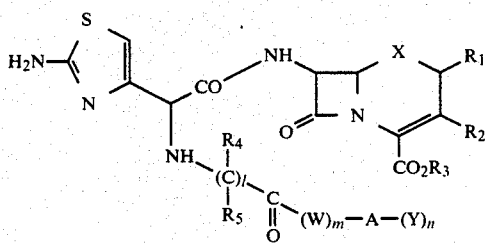

{wherein X is $CH_2$ (methylene group), S (sulfur atom) or O (oxygen atom); Y is a hydroxyl group, a lower alkanoyloxy group or a lower alkoxycarbonyloxy group;. W is a group represented by $CH_2$, NH,

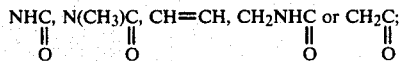

A is a phenyl group, a naphthyl group, or a chromonyl group, respectively substituted by $(Y)_n$; $R_1$ is a hydrogen atom, a hydroxyl group, a methoxy group or a lower alkyl group; $R_2$ is a hydrogen atom, a halogen atom, a methoxy group or a group represented by $CH_2R_2'$ [wherein $R_2'$ is a hydrogen atom, an azido group, a lower alkanoyloxy group, a carbamoyloxy group, a pyridinium group, a substituted pyridinium group or a substituted or unsubstituted heterocyclic thio group (where the term "heterocyclic" means a 5- or 6-membered heterocyclic group having 1 to 4 hetero atoms of O, S, and N)]; $R_3$ is a hydrogen atom, an alkali metal, an alkaline earth metal, an organic ammonium group or an ester residue; $R_4$ and $R_5$ each are a hydrogen atom, a lower alkyl group or a cycloalkylidene group with a carbon atom combined therewith; l is 0 or an integer of 1, 2 or 3; m is 0 or 1; and n is an integer of 1, 2, 3, 4, or 5}, and further relates to (2) a novel carboxylic acid represented by the general formula (III):

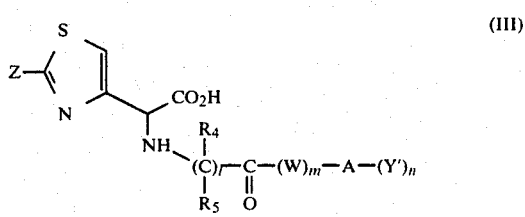

(wherein Z is an amino group or a protected amino group, Y' is the group defined above by Y as well as a protected hydroxyl group, and A, W, $R_4$, $R_5$, l, m and n have the same meanings as defined above) or its reactive derivative.

In the definition of Y in the general formula (I), the lower alkanoyloxy group means a straight or branched lower alkanoyloxy group having 1 to 6 carbon atoms, and the lower alkoxycarbonyloxy group means a lower alkoxycarbonyloxy group having 2 to 5 carbon atoms.

In the definition of $R_1$, the lower alkyl group means a straight or branched lower alkyl group having 1 to 6 carbon atoms. In the definition of $R_2$, the halogen atom includes chlorine, bromine, etc. In the definition of $R_2'$, the lower alkanoyloxy group means a lower alkanoyloxy group having 2 to 6 carbon atoms, and the substituent for the substituted pyridinium group includes —$(CH_2)_p$—$R_A$ (wherein $R_A$ is a carbamoyl group, carboxyl group, cyano group or lower alkoxycarbonyl group having 2 to 5 carbon atoms, and p is 0, 1, 2 or 3), and —$R_B$—$SO_3$—$R_C$ (wherein $R_B$ is a lower alkylene group having 1 to 3 carbon atoms, and $R_C$ has the same meaning as $R_3$). The substituent for the heterocyclic thio group is exemplified by a lower alkyl group having 1 to 5 carbon atoms, hydroxyl group, oxo group, amino group, nitro group, $(CH_2)_qCO_2H$, $(CH_2)_qCO_2$— (lower alkyl group), $(CH_2)_qSO_3H$, $(CH_2)_q$—N (lower alkyl group)$_2$, etc., where q represents an integer of 1 to 3 and the lower alkyl group means a lower alkyl group having 1 to 4 carbon atoms. The 5- or 6-membered heterocyclic group having 1 to 4 atoms of N, O and S is exemplified by tetrazolyl group, thiadiazolyl group, triazolyl group, triazinyl group, thiazolyl group, etc.

In the definition of $R_3$, the alkali metal and alkaline earth metal are metals capable of forming a counter-cation to carboxylate anion ($COO^-$), and the former is exemplified by sodium, potassium, etc., whereas the latter is exemplified by magnesium, calcium, barium, etc. The counter-cation also includes ammonium groups of organic amines such as basic amino acid, etc.

The ester residue represented by $R_3$ is, for example, a group which is relatively readily eliminable in a living body, and is represented by the formula:

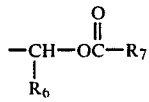

(wherein $R_6$ represents a hydrogen atom or a lower alkyl group having 1 to 6 carbon atoms, and $R_7$ represents a lower alkyl group having 1 to 6 carbon atoms, or phenyl group), or by the formula

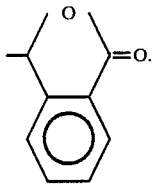

In the definition of $R_4$ and $R_5$, the lower alkyl group represents a lower alkyl group having 1 to 5 carbon atoms, and the cycloalkylidene group means a cycloalkylidene group having 3 to 6 carbon atoms.

In the general formula (III), Z represents an amino group or a protected amino group, and the protective group is exemplified by the ordinary amino-protecting group such as trityl group, formyl group, chloroacetyl group, bromoacetyl group, 2,2,2-trichloroacetyl group, t-butyloxy-carbonyl group and benzyloxycarbonyl group. In the definition of Y', the protective group for the hydroxyl group is exemplified by formyl group, chloroacetyl group, bromoacetyl group, 2,2,2-trichloroethoxycarbonyl group, tetrahydropyranyl group, methoxymethyl group, ethoxyethyl group, trimethylsilyl group, t-butyldimethylsilyl group, etc. When at least two adjacent hydroxyl groups such as in catechol, etc. come into question, the protective group also includes those capable of forming cyclic protected compounds, represented by the following formulae:

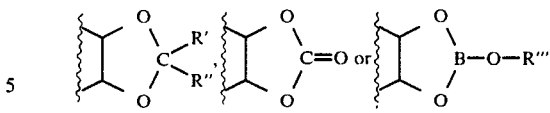

(wherein R' and R" are the same or differnt and represent hydrogen atoms, lower alkyl groups having 1 to 6 carbon atoms or phenyl groups, and R'" represents a hydrogen atom or a lower alkyl group having 1 to 3 carbon atoms).

The reactive derivative of carboxylic acid represented by the general formula (III) is exemplified by an acid halide such as acid chloride and acid bromide, an acid anhydride, mixed acid anhydride such as those with a chlorocarbonic ester, e.g. methyl chlorocarbonate, ethyl chlorocarbonate, isobutyl chlorocarbonate, etc. acid azide, active ester such as nitrophenylthio ester and N-hydroxy-succinic acid ester, etc., and means all the carboxylic acid derivatives capable of forming an acyl compound with the amino group at the 7-position of cephalosporin or its analogs.

The β-lactam compound represented by the general formula (I) can be prepared according to the following procedure A or B.

Procedure A

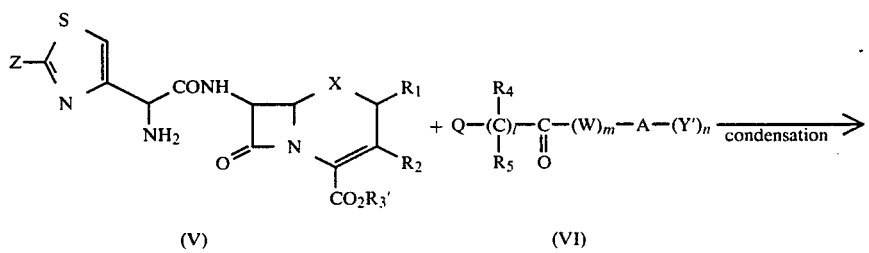

(V)          (VI)

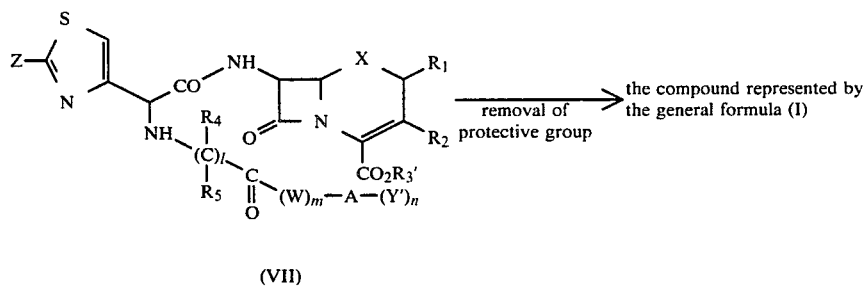

(VII)

[wherein $R_3'$ represents the groups represented by said $R_3$, as well as t-butyl group, benzyl group, p-nitrobenzyl group, benzhydryl group, trityl group or trimethylsilyl group, and when $l \neq 0$, Q represents chlorine, bromine or iodine atom, or a sulfonate group such as mesyloxy group and tosyloxy group, and when $l=0$, the compound of the formula (VI) represents a reactive derivative of a corresponding carboxylic acid as

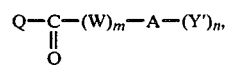

and the reactive derivative is exemplified by an acid halide, acid anhydride (including those formed from carbodiimide, etc.), mixed acid anhydride, active ester, etc., and X, Y', Z, A, W, $R_1$, $R_2$, $R_3'$, $R_4$, $R_5$, m and n have the same meanings as defined above].

As the acid halide, mixed acid anhydride and active ester, similar ones as described in respect of the compound of the formula (III) are exemplified.

The first step is a step of condensing an amino compound represented by the general formula (V) with a reactive alkylating agent represented by the general formula (VI) ($l \neq 0$) or an acylating agent ($l=0$). The condensation can be carried out, if necessary, in the presence of a base in a solvent at a temperature of $-50°$ to $+50°$ C.

The amino compound (V) can be used as such, or as an inorganic acid salt such as hydrochloride, hydrobromide and phosphate, an organic acid salt such as trifluoro-acetate and methanesulfonate, or an N-silyl derivative. The acylation (condensation) reaction is carried out in an aqueous solvent or a non-aqueous solvent, if necessary, in the presence of a base or other acid-capturing agents. As the solvent, halogenated hydrocarbon such as methylene chloride, ether such as tetrahydrofuran, ester such as ethyl acetate, amide such as dimethylformamide, sulfoxide such as dimethylsulfoxide, acetonitrile, acetone, water, etc., can be used alone or in combination.

Organic tertiary amine such as triethylamine and dimethylaniline, and inorganic base such as sodium bicarbonate and potassium carbonate can be used as the base, and oxirane compound such as ethylene oxide and propylene oxide can be used as the acid-capturing agent.

Among the compounds represented by the general formula (V), the compounds whose X is S can be prepared according to the procedure disclosed in J. Antibiotics 35 1022 (1980). The oxacephalosporines, whose X is O, can be prepared by synthesizing a 7-amino compound according to the procedures disclosed in J. Med. Chem., 20 551 (1977), ibid. 22 757 (1979), J. Am. Chem. Soc., 101 4403 (1979), etc., and then by synthesizing a corresponding compound represented by the general formula (V) therefrom according to the procedure for preparing cephalosporines (X=S).

Among carbacephems, whose X is $CH_2$, those of which nucleus is dl-form can be prepared according to the procedure disclosed in Japanese Published Unexamined Patent Application No. 9782/1982, and those of which nucleus is optically active can be prepared according to the procedure disclosed in detail hereinafter as Reference Examples.

A group of the compounds represented by the general formula (VI) are known and disclosed in Chem. Ber. 61B 791 (1928), etc.

The second step is a step of removing the protective group, and can be carried out by removing the protective group for the functional groups (hydroxyl group, amino group and carboxyl group) in Z, Y' and $R_3'$ according to the ordinary procedure after isolation and purification of the intermediate (VII) [the compounds represented by the general formula (I), (II), . . . are hereinafter referred to as Compound (I), Compound (II), . . . , respectively or referred to merely as (I), (II), . . . , respectively, in some cases] or without the isolation and purification.

The protective groups for the hydroxyl group, amino group and carboxyl group can be respectively removed by a suitable method described in detail in McOmie: "Protective Groups in Organic Chemistry" (1973, Plenum Press), Chapters 2, 3, 4 and 5.

In the case of $l=0$ and W being the group of

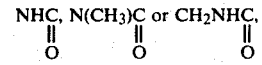

the corresponding Compound (I') can also be prepared according to the following formulae:

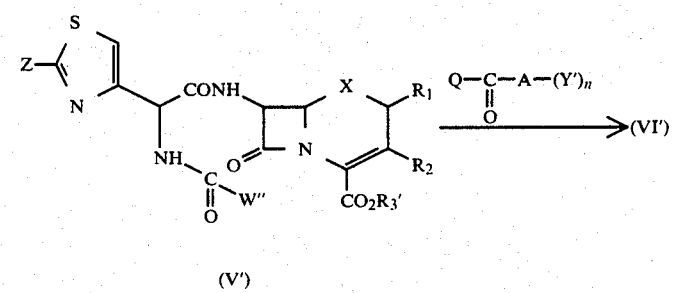

(V')

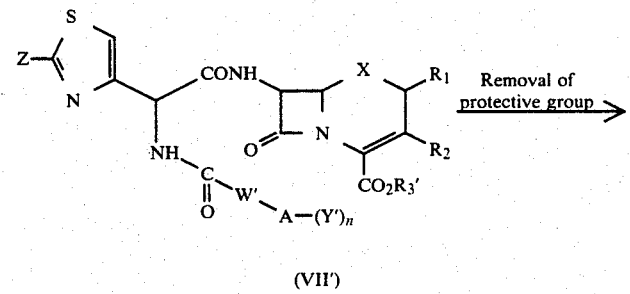

(VII')

-continued

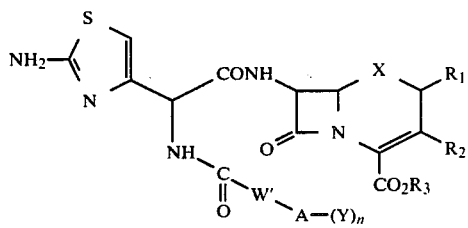

(I')

(wherein W' represents a group of

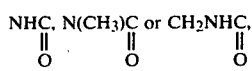

W''' represents a group of $NH_2$, $NHCH_3$ or $CH_2NH_2$, and X, Y, Y', Z, A, $R_1$, $R_2$, $R_3$, $R_3'$, Q and n have the same meanings as defined above).

The compound represented by the general formula (V') wherein $X=CH_2$ can be prepared according to the procedure disclosed in Reference Example, and compound (V') wherein $X=S$ or $O$ can also be prepared in a similar manner.

The compound represented by the general formula (VI') is known, and is disclosed in Chem. Ber. 61B 791 (1928), etc.

In the case of W being the group of NH or

and $l=0$, the corresponding compound (I'') can be prepared according to the following formulae:

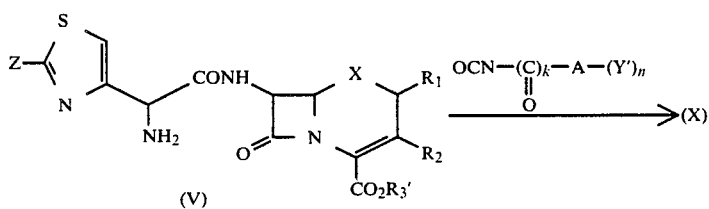

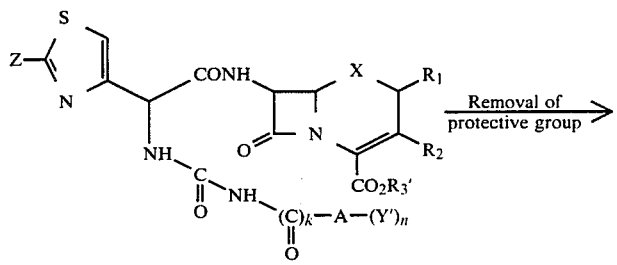

(VII'')

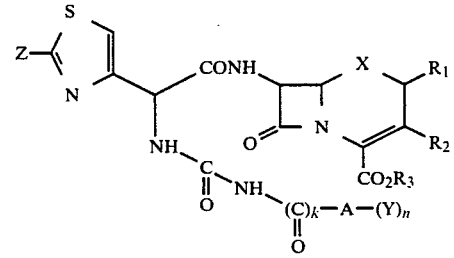

(I'')

(wherein k is 0 or 1, and X, Y, Y', Z, A, $R_1$, $R_2$, $R_3$, $R_3'$ and n have the same meanings as defined above).

The compound represented by the general fromula (I) has an asymmetrical center at the $\alpha$ position (marked by *) and therefore an L isomer and a D isomer exist. Each isomer can be prepared according to the following procedure (a), (b) or (c).

The compound represented by the general formula (X) is known and disclosed in Japanese Published Unexamined Patent Application No. 40687/1981, etc.

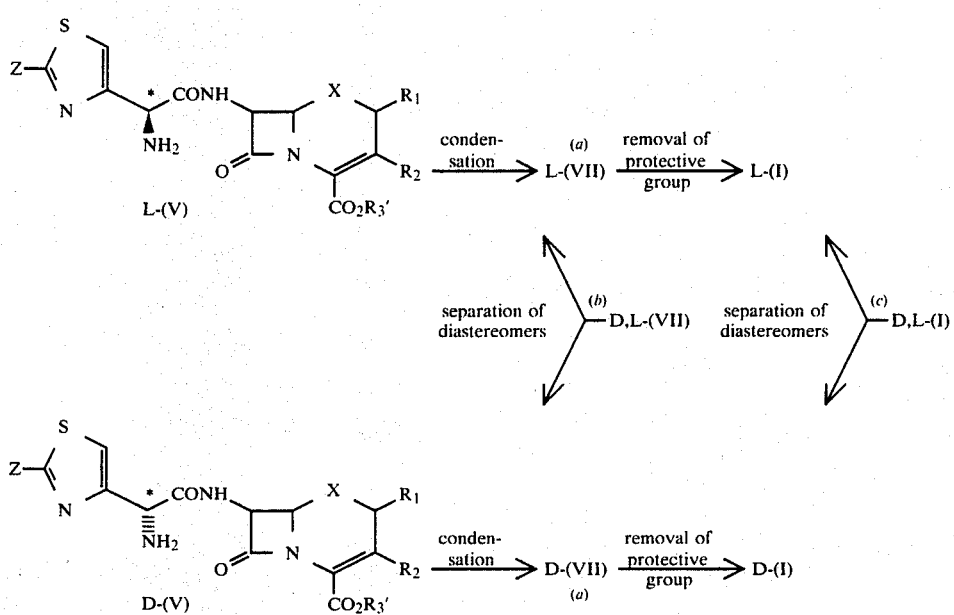

(wherein X, Z, $R_1$, $R_2$ and $R_3'$ have the same meanings as defined above).

Procedure (a): Through the said steps of condensation and removal of the protective group, L-(I) compound and D-(I) compound can be derived from the corresponding starting L-(V) compound and D-(V) compound, respectively, which have been resolved at the stage of amino compound (V) in advance. The procedure for preparing the starting compounds L-(V) and D-(V) is partly disclosed in the said literature regarding the compound (V), and they are prepared according to the following reference formulae:

Reference formulae

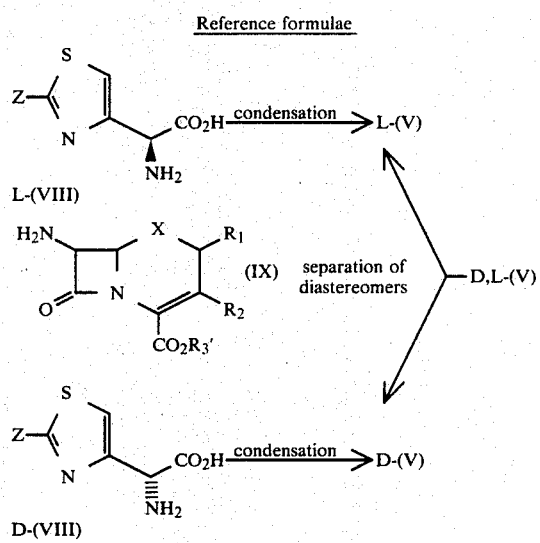

(wherein X, Z, $R_1$, $R_2$ and $R_3'$ have the same meanings as defined above).

The compound D-(VIII) can be prepared according to the procedure disclosed in Japanese Published Unexamined Patent Application No. 9782/1982 and the compound LO(VIII) can be prepared according to the procedure given in Reference Examples of the present specification.

Among the compounds represented by the general formula (IX), the cephalosporins, whose X is S, are well known compounds, and the oxacephalosporins, whose X is O, can be prepared according to the procedures disclosed in J. Med. Chem., 20 551 (1977), ibid., 22 757 (1979), J. Am. Chem. Soc., 101 4403 (1979), etc. The carbacephems, whose X is $CH_2$, can be prepared according to the procedures disclosed In GB No. 2017102A, GB No. 2017103A, U.S. patent application Ser. No. 107,435 filed on Dec. 26, 1979, EP No. 0014475A1, EP No. 0027882A1, etc.

Procedure (b): The D,L-(VII) compound, a mixture of D and L isomers, at the α position, is a mixture of two diastereoisomers L-(VII) and D-(VII) having different physical properties such as optical rotation, etc., and thus can be separated into the two isomers by chromatography using silica gel, alumina, ionic or hydrophobic resin, or the like as a carrier, or by fractional crystallization.

The separated L-(VII) and D-(VII) isomers can be converted to the corresponding L-(I) and D-(I) compounds by removing the protective groups, respectively.

Procedure (c): L-(I) and D-(I) can also be prepared from D,L-(I) by diastereomer separation in the final stage in the similar manner as the procedure (b).

Procedure B carboxylic acid represented by the general formula (III) or its reactive derivative + 7-amino compound represented by the general formula (IX) $\xrightarrow{\text{condensation}}$

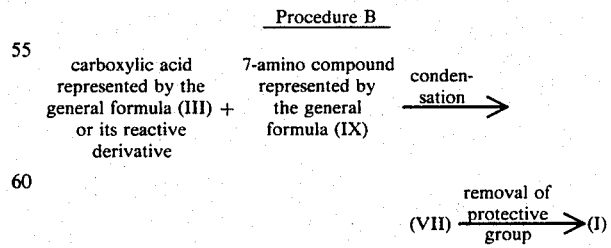

Condensation in the first step is carried out by the ordinary procedure for acylation of penicillin and cephalosporin, for example, an acid halide procedure, acid anhydride procedure (including a dicyclohexylcarbodiimide procedure), mixed acid anhydride procedure, active ester procedure and acid azide procedure, among which the mixed acid anhydride procedure is preferable. Typical mixed acid anhydrides of the compound (III) are anhydrides formed from the compound (III) and chlorocarbonate ester such as methyl chlorocarbonate, ethyl chlorocarbonate and isobutyl chlorocarbonate in the presence of a base.

The 7-amino compound (IX) can be used as such, or as an inorganic acid salt such as hydrochloride, hydrobromide and phosphate, an organic acid salt such as trifluoroacetate and methanesulfonate, or an N-silyl derivative. The acylation (condensation) reaction is carried out in an aqueous or non-aqueous solvent at a temperature of −50° to 50° C., if necessary, in the presence of a base or other acid-capturing agents. As the solvent, halogenated hydrocarbon such as methylene chloride, ether such as tetrahydrofuran, ester such as ethyl acetate, amide such as dimethylformamide, sulfoxide such as dimethylsulfoxide, acetonitrile, acetone, water, etc., can be used alone or in combination.

Organic tertiary amine such as triethylamine and dimethylaniline, and inorganic base such as sodium bicarbonate and potassium carbonate can be used as the base, and oxirane compound such as ethylene oxide and propylene oxide can be used as the acid-capturing agent.

The compound represented by the general formula (I) wherein Y is a hydroxyl group can also be prepared by hydrolyzing the corresponding lower acyloxy compound such as an acetoxy compound with methanol-ammonia, a dilute aqueous alkaline solution of sodium bicarbonate, etc.

The compound represented by the general formula (III) can be prepared according to the following procedure:

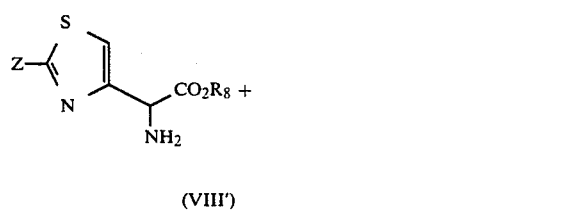

(VIII')

compound represented by the general formula (VI) $\xrightarrow{\text{condensation and, if necessary, removal of carboxy-protecting group}}$ compound represented by the general formula (III)

(wherein $R_8$ represents a hydrogen atom or a protective group for the carboxyl group, and Z has the same meaning as defined above).

The condensation reaction can be carried out in the same manner as in the process for preparing the compound represented by the general formula (I), procedure A. In the case of $l \neq 0$, Q represents a chlorine, bromine or iodine atom, or sulfonate group such as mesyloxy group and tosyloxy group. In the case of $l=0$, the compound (VI) represents a reactive derivative of a corresponding carboxylic acid as

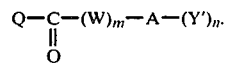

The reactive derivative includes acid halide, acid anhydride (including those formed by carbodiimide, etc.), mixed acid anhydride, active ester, etc. Condensation is carried out in the same solvent as used in the said procedure A at a temperature of −50° to +50° C., if necessary, in the presence of a base.

When W is a group represented by

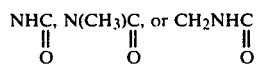

in the general formula (III), the corresponding compound (III') can be produced according to the following formulae:

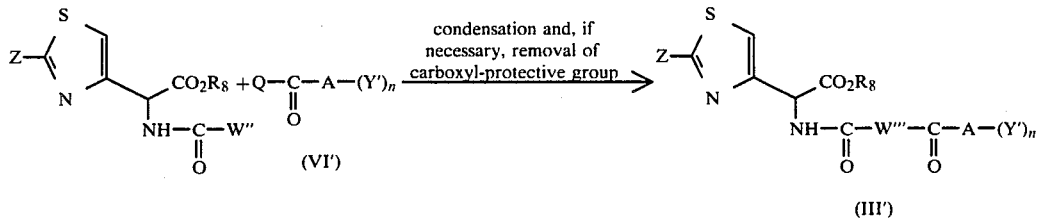
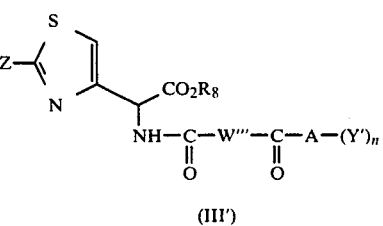

(III')

(wherein W" has the same meaning as defined above, W"" is NH, N(CH$_3$) or CH$_2$NH, and Y', Z, A, Q, $R_8$ and n have the same meanings as defined above).

In the case of $l=0$ and W being the group of NH or $$\underset{O}{\overset{\|}{N H C,}}$$

the corresponding compound (III") represented by the general formula (III") can also be prepared according to the following formulae:

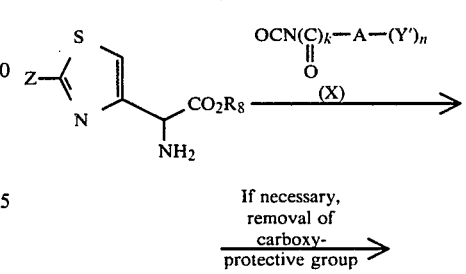

$\xrightarrow{\text{If necessary, removal of carboxy-protective group}}$

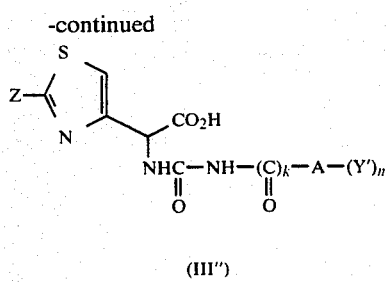

(III″)

(wherein Y', Z, A, R$_8$, k and n have the same meanings as defined above).

The protective group R$_8$ for a carboxyl group is exemplified by a group relatively easily removable by an alkali, acid or Lewis acid, that is, lower alkyl groups such as methyl, ethyl and t-butyl, and arylmethyl groups such as benzyl, p-methoxybenzyl, p-nitrobenzyl, diphenyl-methyl and triphenylmethyl. In the case of $l=0$ and $m=1$, t-butyl, benzyl, p-methoxybenzyl, p-nitrobenzyl, diphenyl-methyl, triphenylmethyl, etc., which are removable by an acid or a Lewis acid, can be used.

The reaction of removing the carboxyl-protective group can be carried out at a temperature of $-50°$ to $+50°$ C. under the ordinary conditions for the ester elimination reaction. Of course, the present condensation reaction can also be carried out using a free carboxylic acid whose R$_8$ is a hydrogen atom.

By using L(VIII') and D-(VIII') resolved with respect to the asymmetrical center at the α position of compound (VIII'), the corresponding L-(III) and D-(III) can be prepared, if desired, and the said procedure B can be applied to these compounds to prepare the corresponding L-(I) and D-(I) as an alternative procedure to the said procedures (a), (b) and (c).

The compounds of the present invention have a strong antibacterial activity against Gram-positive and Grae-negative bacteria, and are useful for curing various infections, as a sterilizer and as an antiseptic component.

Thus, the invention includes within its scope pharmaceutical compositions comprising, as an active ingredient, a β-lactam compound represented by the general formula (I) or a pharmaceutically acceptable salt thereof in association with a pharmaceutical carrier or diluent. The compounds of this invention are administered by parenteral (intramuscular, intraperitoneal, intravenous or subcutaneous injection routes), oral or rectal route of administration and can be formulated in dosage forms appropriate for each route of administration.

Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions or by heating the compositions. They can also be manufactured in the form of sterile solid compositions which can be dissolved in sterile water or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth or polyvinyl-pyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agent such as sodium lauryl sulfate. The tablets may be coated according to methods well known in the art. Oral liquid preparations may be in the form of aqueous or oily suspension, solution, emulsions, syrups, etc., or may be presented as a dry product, for reconstitution with water or other suitable vehicle before use. Such liquid preparations may contain conventional additive such as suspending agents, for example, sorbitol syrup, methyl cellulose, glucose sugar syrup, gelatin, hydroxy-ethyl-cellulose, carboxymethylcellulose, aluminum stearate gel, emulsifying agents, for example, lecithin or sorbitan monooleate; non-aqueous vehicles, which may include edible oils, for example, almond oil, coconut oil, propylene glycol or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 5 and 350 mg/kg of body weight daily are administered to mammalian patients to achieve an antibiotic effect.

The present invention is described in detail, referring to Examples and Reference Examples. In the following description of absolute structure, D- and L-isomers at the said α position is represented by (R) and (S), respectively.

EXAMPLE 1

Preparation of (6R, 7S)-7-{2-(2-aminothiazol-4-yl)-2-[3-(3,4-diacetoxybenzoyl)-1-ureido]acetamido}-1-azabicyclo[4,2,0]oct-2-en-8-oxo-2-carboxylic acid:

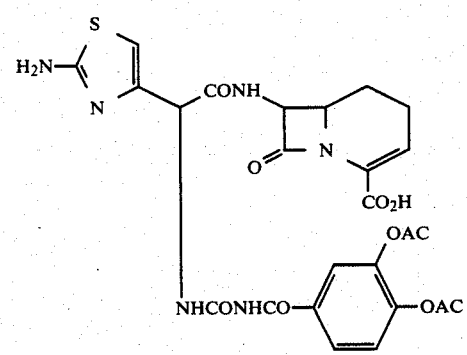

At first, 200 mg of 3,4-diacetoxybenzamide is dissolved in 2 ml of 1,2-dichloroethane, and 0.186 ml of oxazolyl chloride is added thereto with ice cooling. The mixture is refluxed with heating for 8 hours and 30 minutes. The reaction mixture is cooled and then concentrated under reduced pressure. The residue is dissolved in 2 ml of methylene chloride to prepare a solution of 3,4-diacetoxy-benzoyl isocyanate. Then, 160 mg of (6R, 7S)-7-[2-(2-aminothiazol-4-yl)-2-aminoacetamido]-1-azabicyclo[4,2,0]oct-2-en-8-oxo-2-carboxylic acid hydrochloride obtained in Reference Example 2 is suspended in 2 ml of methylene chloride, and 1.2 ml of N,O-bistrimethylsilylacetamide is added thereto to dissolve the hydrochloride. The said solution of 3,4-diacetoxybenzoyl isocyanate is added to the solution, and the mixture is stirred at room temperature overnight. Then, 1 ml of methanol is added to the reaction mixture, and the resulting mixture is concentrated under reduced pressure. The residue is dissolved in 1 ml of dimethylsulfoxide, and the solution is purified by column chromatography with 50 ml of Diaion HP-10 (adsorption resin made by Mitsubishi Chemical Industries Ltd.) (eluting solvent methanol:water=5:1), whereby 143 mg of white powder is obtained. The powder has the following physical properties and is identified to be the desired compound. Yield: 55.6%.

NMR*(DMSO-d$_6$-CD$_3$OD) δ: 7.8–7.2 (3H, m), 6.55 (1H, bs), 6.32 (1H, m), 5.53, 5.49 (1H, s), 5.42, 5.32 (1H, d), 3.8 (1H, m), 2.29 (6H, s), 2.2 (2H, m), 1.6 (2H, m).
* The compound is a mixture of diastereomers, where signals originating from the individual isomer are present as mixed. The same shall apply hereinafter.

IR $\nu_{max}$cm$^{-1}$ (KBr): 1795, 1790, 1775, 1770, 1720, 1700, 1685, 1540, 1530.

EXAMPLE 2

Preparation of (6R, 7S)-7-{2-(2-aminothiazol-4-yl)-2-[3-(3,4-dihydroxybenzoyl)-1-ureido]acetamido}-1azabicyclo[4,2,0]oct-2-en-8-oxo-2-carboxylic ac id:

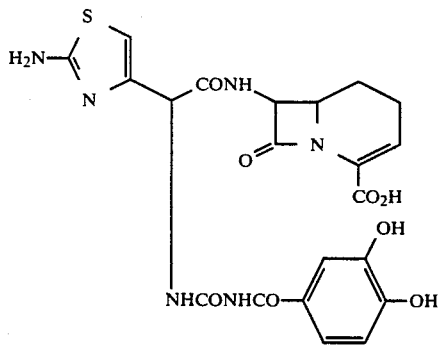

At first, 5 ml of methanol and 60 μl of 28% aqueous ammonia are added to 92 mg of (6R, 7S)-7-{2-(2-aminothiazol-4-yl)-2-[3-(3,4-diacetoxybenzoyl)-1-ureido]acetamido}-1azabicyclo[4,2,0]oct-2-en-8-oxo-2-carboxylic acid to obtain a solution, and the solution is subjected to reaction at room temperature for 30 minutes. Then, the reaction mixture is adjusted to pH 3 with 1 N hydrochloric acid, and concentrated under reduced pressure. Then, 0.5 ml of water is added to the residue, and the mixture is adjusted to pH 8.0 with a saturated aqueous sodium bicarbonate solution to obtain a solution. Then, the solution is subjected to purification by column chromatography with 30 ml of Diaion HP-10 (eluting solvent water:methanol=5:2), whereby 79 mg of white powder is obtained. The powder has the following physical properites and is identified to be the sodium salt of the desired compound. Yield: 95.8%.

NMR*(D$_2$O) δ: 7.4–6.8 (3H, m), 6.68 (1H, bs), 6.14 (1H, m), 5.38 (1H, bs), 5.29, 5.20 (1H, d), 3.8 (1H, m), 2.3 (2H, m), 1.6 (2H, m).
* The same shall apply hereinafter.

EXAMPLE 3

Preparation of (6R, 7S)-7-[2-[2-aminothiazol-4-yl)-2-(3,4-diacetoxybenzamido]acetamido]-1-azabicyclo[4,2,0]-oct-2-en-8-oxo-2-carboxylic acid:

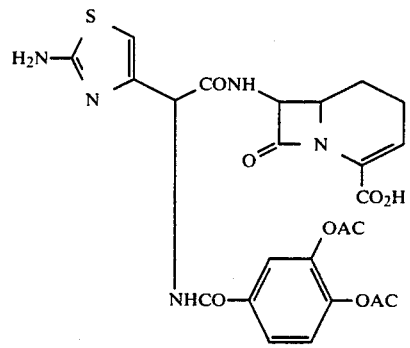

At first, 180 mg of (6R, 7S)-7-[2-(2-aminothiazol-4-yl)-2-aminoacetamido]-1-azabicyclo[4,2,0]oct-2-en-8-oxo-2-carboxylic acid hydrochloride obtained in Reference Example 2 is suspended in 2 ml of tetrahydrofuran, and then 1.3 ml of N,O-bistrimethylsilylacetamide is added thereto to obtain a solution. Then, 123.5 mg of 3,4-diacetoxybenzoyl chloride is added thereto, and the mixture is subjected to reaction at room temperature for 1 hour. Then, the reaction mixture is concentrated, and the residue is dissolved in 2 ml of dimethylsulfoxide and 0.2 ml of water. The solution is subjected to purification by column chromatography with 30 ml of Diaion HP-10 (eluting solvent water:methanol=1:2), whereby 204 mg of white powder is obtained. The powder has the following physical properties, and is identified to be the desired compound. Yield: 76.0%.

NMR*(DMSO-d$_6$-CD$_3$OD) δ: 7.83–7.33 (3H, m), 6.63 (1H, s), 6.34 (1H, m), 5.64, 5.61 (1H, s), 5.37 (1H, m), 2.3 (6H, s), 2.2 (2H, m), 1.6 (2H, m).

IR $\nu_{max}$cm$^{-1}$ (KBr): 3460, 1790, 1770, 1645.

EXAMPLE 4

Preparation of (6R, 7S)-7-[2-(2-aminothiazol-4-yl)-2-(3,4-dihydroxybenzamido) acetamido]-1-azabicyclo[4,2,0]oct-2-en-8-oxo-2-carboxylic acid:

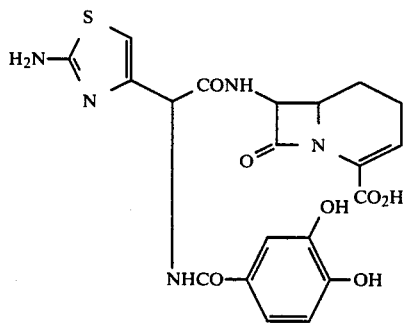

In this example, 98 mg of the compound obtained in Example 3 is treated in the same manner as in Example 2 to obtain 74 mg of the sodium salt of the desired compound. Yield: 85.0%.

NMR*(D$_2$O) δ: 7.39–6.94 (3H, m), 6.78 (1H, s), 6.18 (1H, m), 5.59 (1H, s), 5.44, 5.34 (1H, d), 4.01–3.81 (1H, m), 2.44–1.35 (4H, m).

IR $\nu_{max}$cm$^{-1}$ (KBr): 3420, 1770, 1750, 1640, 1605, 1520.

EXAMPLE 5

The following compounds are obtained according to the same procedures as in Example 3, except that the following acid chlorides are used in place of 3,4-diacetoxybenzoyl chloride as used in Example 3. These compounds can be converted to the corresponding hydroxy compounds in the same manner as in Example 2.

| Acid chloride used | Compound obtained | Yield | NMR* δ | IR$\nu_{max}^{cm^{-1}}$ (KBr) |
|---|---|---|---|---|
| 2,3-diacetoxy benzoyl chloride | (6R, 7S)—7-[2-(2-aminothiazol-4-yl)-2-(2,3-diacetoxybenzamido)acetamido]-1-azabicyclo[4,2,0]-oct-2-en-8-oxo-2-carboxylic acid (5-1)* | 60.2% | (DMSO—d$_6$—CD$_3$OD): 7.8–7.4(3H,m) 6.53(1H,bs), 6.30(1H,m), 5.53, 5.48(1H,s), 5.38, 5.28(1H,d), 3.75(1H,m), 2.27(6H,s), 2.3(2H,m), 1.6(2H,m) | |
| | (6R, 7S)—7-[2-(2-aminothiazol-4-yl)-2-(2,3-dihydroxybenzamido)acetamido]-1-azabicyclo[4,2,0]-oct-2-en-8-oxo-2-carboxylic acid (5-2)* | 75.8% | (D$_2$O): 7.3–6.7(3H,m), 6.66(1H,bs), 6.09(1H,m), 5.52(1H,bs), 5.31, 5.25(1H,d) 3.7(1H,m), 2.2(2H,m), 1.6(2H,m) | 3200, 1770 1750, 1665, 1645, 1595 1505 |
| 3,5-diacetoxy benzoyl chloride | (6R, 7S)—7-[2-(2-aminothiazol-4-yl)-2-(3,5-diacetoxybenzamido)acetamido]-1-azabicyclo[4,2,0]-oct-2-en-8-oxo-2-carboxylic acid (5-3)* | 54.8% | (DMSO—d$_6$—D$_2$O): 7.6(2H,m), 7.2(1H,m), 6.52(1H,s), 6.32 (1H,m), 5.56, 5.53(1H,s), 5.39, 5.32(1H,d), 2.30(6H,s), 2.2(2H, m), 1.6(2H,m) | 3310, 1780 1770, 1760 1670, 1625 1590, 1540 |
| | (6R, 7S)—7-[2-(2-aminothiazol-4-yl)-2-(3,5-dihydroxybenzamido)acetamido]-1-azabicyclo[4,2,0]oct-2-en-8-oxo-2-carboxylic acid (5-4)* | 92.4% | (D$_2$O): 6.7(2H,m), 6.62(1H,s) 6.5(1H,m), 5.47(1H,s), 5.28, 5.20(1H,d), 3.75(1H,m), 2.2(2H,m), 1.5(2H,m) | 3300, 1770 1750, 1640 1595, 1520 |
| 3,4,5-triacetoxy benzoyl chloride | (6R, 7S)—7-[2-(2-aminothiazol-4-yl)-2-(3,4,5-triacetoxybenzamido)acetamido]-1-azabicyclo[4,2,0]-oct-2-en-8-oxo-2-carboxylic acid (5-5)* | 58.3% | (DMSO—d$_6$—CD$_3$OD): 7.78(2H,s), 6.50(1H,s), 6.30(1H,m), 5.60, 5.57(1H,s), 5,41, 5.33(1H,d) 3.8(1H,m), 2.30(9H,s), 2.2 | 3280, 1795 1790, 1770 1760, 1645 1560, 1540 |

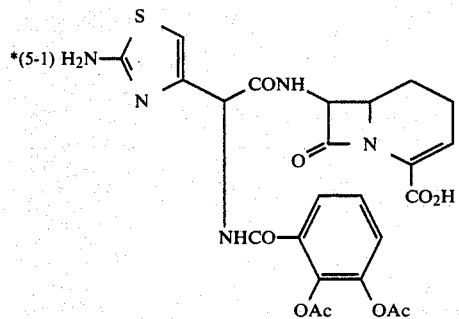

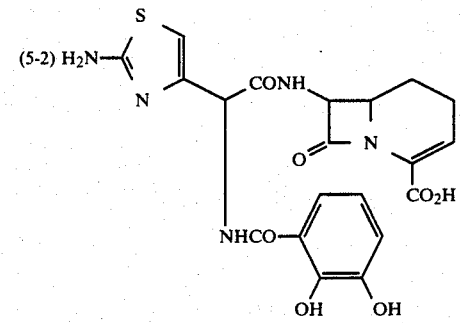

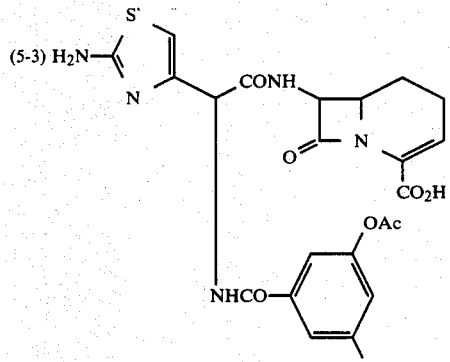

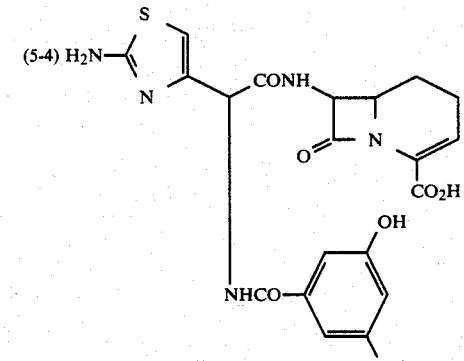

(5-5) 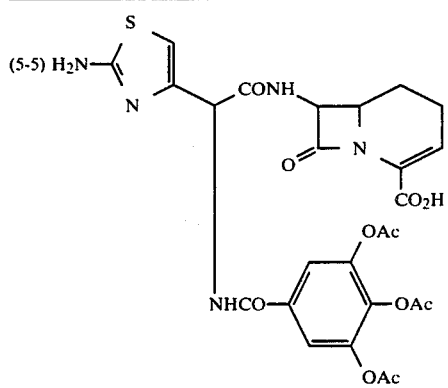

EXAMPLE 6

Preparation of (6R, 7S)-7-[(S)-2-(2-aminothiazol4-yl)-2-(3,4-diacetoxybenzamido) acetamido]-1-azabicyclo-[4,2,0]oct-2-en-8-oxo-2-carboxylic acid:

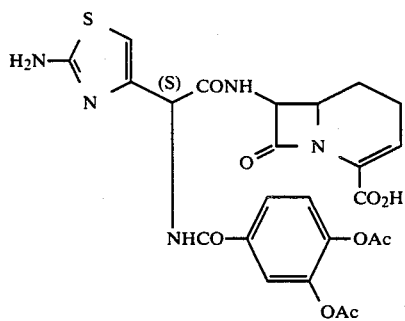

According to the same procedures as in Example 3 except that 180 mg of (6R, 7S)-7-[(S)-2-(2-aminothiazol-4-yl)-2-aminoacetamido]-1-azabicyclo[4,2,0]-oct-2-en-8-oxo-2carboxylic acid hydrochloride obtained in Reference Example 4 is used in place of the compound obtained in Reference Example 2, 194 mg of white power is obtained. The powder has the following physical properties and is identified to be the desired product. Yield: 72.3%.

NMR (DMSO-$d_6$-CD$_3$OD) δ: 7.8 (2H, m), 7.35 (1H, d), 6.57 (1H, s), 6.39 (1H, m), 5.60 (1H, s), 5.37 (1H, d), 3.8 (1H, m), 2.30 (6H, s), 2.2 (2H, m), 1.6 (2H, m).

IR $\nu_{max}^{cm-1}$ (KBr): 1785, 1775, 1760, 1700, 1645, 1545.

EXAMPLE 7

Preparation of (6R, 7S)-7-[(R)-2-(2-aminothiazol-4-yl)-2-(3,4-diacetoxybenzamido) acetamido]-1-azabicyclo-[4,2,0]-oct-2-en-8-oxo-2-carboxylic acid:

According to the same procedures as in Example 3, except that 180 mg of (6R, 7S)-7-[(R)-2-(2-aminothiazol-4-yl)-2-aminoacetamido]-1-azabicyclo-[4,2,0]-oct-2-en-8-oxo-2-carboxylic acid hydrochloride obtained in Reference 3 is used in place of the compound obtained in Reference 2 and used in Example 3, 210 mg of white powder is obtained. The powder has the following physical properties and is identified to be the desired compound. Yield: 78.3%.

NMR (DMSO-$d_6$-CD$_3$OD) δ: 7.7 (2H, m), 7.34 (1H, d), 6.58 (1H, s), 6.39 (1H, m), 5.63 (1H, s), 5.43 (1H, d), 3.79 (1H, m), 2.30 (6H, s), 2.2 (2H, m), 1.6 (2H, m).

IR $\nu_{max}^{cm-1}$ (KBr) 1790, 1775, 1760, 1655, 1530.

EXAMPLE 8

Preparation of (6R, 7S)-7-[2-(2-aminothiazol-4-yl)2-(6,7-diacetoxychromone-3-carboxyamido) acetamido]-1azabicyclo[4,2,0]-oct-2-en-8-oxo-2-carboxylic acid:

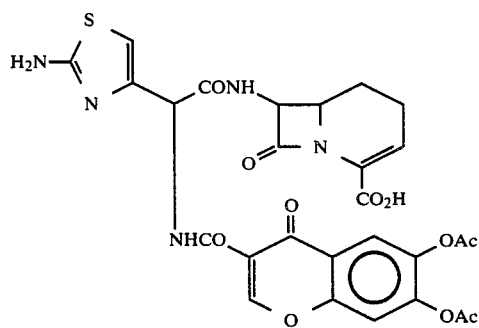

At first, 67.4 mg of (6R, 7S)-7-[2-(2-aminothiazol-4-yl)-2-aminoacetamido]-1-azabicyclo[4,2,0]-oct-2-en-8-oxo-2-carboxylic acid hydrochloride is suspended in 2 ml of tetrahydrofuran at 0° C., and 0.6 ml of N,O-bis(-trimethylsilyl) acetamide is added thereto with stirring. The mixture is stirred at room temperature for 30 minutes, and then cooled to 0° C. Then, 55.5 mg of 6,7-diacetoxychromone-3-carbonyl chloride is added thereto, and the mixture is stirred at 0° C. for 30 minutes and then at room temperature for 1 hour. Then, 100 ml of ethyl acetate is added thereto, and the mixture is washed with 15 ml of water and then twice with 15 ml of a saturated aqueous sodium chloride solution. The organic layer is dried with anhydrous sodium sulfate, and concentrated to 10 ml under reduced pressure. The deposited crystals are separated by filtration, washed with ethyl acetate, and dried to obtain 50 mg of the desired compound (yield: 47%).

NMR*(DMSO d$_6$) δ: 9.91–9.85 (1H, m), 9.05 (1H, s), 8.98–8.89 (1H, m), 8.04 (1H, s), 7.86 (1H, s), 7.05 (2H, bs), 6.50 (1H, s), 6.29 (1H, m), 5.6–5.2 (2H, m), 2.35 (6H, s), 2.50–1.35 (4H, m).

IR $\nu_{max}^{cm-1}$ (KBr) 3300, 1780, 1760, 1675, 1620, 1530.

EXAMPLE 9

Preparation of (6R, 7S)-7-[2-(2-aminothiazol-4-yl)-2-(6,7-dihydroxychromone-3-carboxyamido)acetamido-1-azabicyclo-[4,2,0]-oct-2-en-8-oxo-2-carboxylic acid:

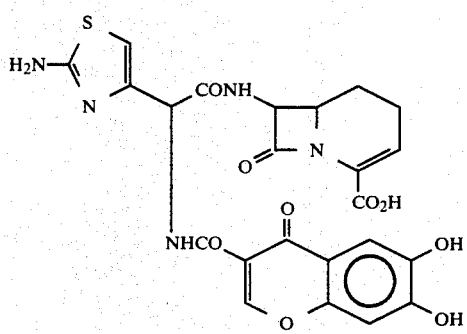

At first, 67.4 mg of (6R, 7S)-7-[2-(2-aminothiazol-4-yl)-2-aminoacetamido]-1-azabicyclo[4,2,0]-oct-2-en-8-oxo-2-carboxylic acid hydrochloride is suspended in 2 ml of tetrahydrofuran at 0° C., and 0.6 ml of N,O-bis(-trimethylsilyl) acetamide is added thereto with stirring. The mixture is stirred at room temperature for 30 minutes, and cooled to 0° C. Then, 41.1 mg of 6,7-dihydroxychromone-3-carbonyl chloride is added thereto, and the mixture is stirred at 0° C. for 30 minutes and then at room temperature for one hour. Then, 100 ml of ethyl acetate is added thereto, and the mixture is washed with 15 ml of water and then twice with 15 ml of a saturated aqueous sodium chloride solution. The organic layer is dried with anhydrous sodium sulfate, and the solvent is distilled off. The residue is dissolved in an aqueous sodium bicarbonate solution, and the solution is purified by Sephadex LH-20 (Pharmacia Fine Chemicals, Inc.) (eluting solvent water:methanol=1:1), whereby 51.0 mg of the desired compound is obtained as a sodium salt (yield: 53%).

NMR*(D$_2$O) δ: 8.36 (1H, s), 6.90 (1H, s), 6.65 (1H, s), 6.4 (1H, bs), 6.1 (1H, m), 5.36 (1H, s), 5.30, 5.23 (1H, d), 3.76 (1H, m), 2.2 (2H, m), 1.6 (2H, m).

IR $\nu_{max}^{cm-1}$ (KBr): 3300, 1770, 1750, 1660, 1600, 1520.

EXAMPLE 10

Preparation of (6R, 7S)-7-[2-aminothiazol-4-yl)-2-(3,4-dihydroxycinnamamido) acetamido]-1-azabicyclo[4,2,0]-oct-2-en-8-oxo-2-carboxylic acid:

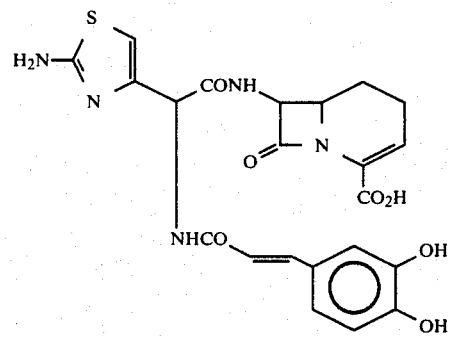

At first, 186.8 mg of (6R, 7S)-7-[2-(2-aminothiazol-4-yl)-2-aminoacetamido]-1-azabicyclo[4,2,0]-oct-2-en-8-oxo-2-carboxylic acid hydrochloride is suspended in 4 ml of tetrahydrofuran at 0° C., and then 1.4 ml of N,O-bis(trimethyl-silyl) acetamide is added thereto with stirring. The mixture is stirred at room temperature for 30 minutes, and cooled to 0° C. Then, 94.4 mg of 3,4-dihydroxycinnamyl chloride is added thereto, and the mixture is stirred at 0° C. for 30 minutes and then at room temperature for one hour. The mixture is concentrated, and sodium bicarbonate is added to the residue. The mixture is subjected to purification by column chromatography with Diaion HP-10 (eluting solvent water:methanol=5:1), whereby 94.0 mg of the desired compound is obtained as a sodium salt (yield: 40%)

NMR*(D$_2$O) δ: 7.43 (1H, d, J=15.6Hz), 7.0 (3H, m), 6.75, 6.72 (1H, s), 6.48 (1H, d, J=15.6Hz), 6.20 (1H, m), 5.53 (1H, s), 5.43, 5.35 (1H, d), 3.9 (1H, m), 2.3 (2H, m), 1.6 (2H, m).

IR $\nu_{max}^{cm-1}$ (KBr): 3410, 1775, 1755, 1665, 1600.

EXAMPLE 11

Preparation of (6R, 7S)-7-[2-(2-aminothiazol-4-yl)-2-(3,4-diacetoxybenzamidoglycinamido) acetamido]-1azabicyclo[4,2,0]]-oct-2-en-8-oxo-2-carboxylic acid:

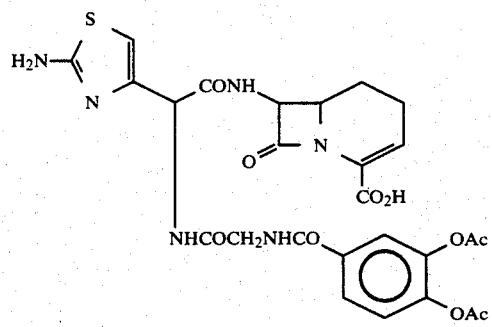

At first, 175 mg of N-t-butoxycarbonylglycine and 115 mg of 1-hydroxybenzotriazole are dissolved in 5 ml of tetrahydrofuran, and then 206 mg of dicyclohexyl-carbodiimide is added thereto with stirring. The mixture is stirred at room temperature for 2 hours, and filtered.

Separately, 373.5 mg of (6R, 7S)-7-[2-(2-aminothiazol-4-yl)-2-aminoacetamido]-1-azabicyclo[4,2,0]- oct-2-en-8-oxo-2-carboxylic acid hydrochloride is dissolved in 10 ml of water and 8 ml of tetrahydrofuran, and the solution is adjusted to pH 8 with a saturated aqueous sodium bicarbonate solution, and cooled to 0° C. Then, the said filtrate is added thereto with stirring, and the mixture is stirred at 0° C. for 30 minutes and further at room temperature for one hour. Tetrahydrofuran is distilled off, and the remaining aqueous solution is subjected to purification by chromatography with Diaion HP-10 (eluting solvent water:methanol =5:1). Then, 5 ml of trifluoroacetic acid is added to the thus obtained compound with ice cooling, and the mixture is stirred at 0° C. for one hour. Then, trifluoroacetic acid is distilled off, and the residue is purified by chromatography with Diaion HP-10 (eluting solvent water:methanol=9:1). Then, 260 mg of the thus obtained compound is suspended in 6 ml of tetrahydrofuran at 0° C., and 1.4 ml of N,O-bis(trimethylsilyl) acetamide is added thereto with stirring. The mixture is stirred at room temperature for 30 minutes and cooled to 0° C. Then, 131.3 mg of 3,4-diacetoxy-benzoyl chloride is added thereto, and the mixture is stirred at 0° C. for 30 minutes and then at room temperature for one hour. Then, tetrahydrofuran is distilled off, and dimethylsulfoxide and water are added to the residue. The mixture is subjected to purification by chromatography with Diaion HP-10 (eluting solvent water:methanol=1:2), whereby 107 mg of the desired compound is obtained (yield: 17%).

NMR*(DMSO d$_6$) δ: 8.8 (1H, m), 7.85–7.33 (3H, m), 6.9 (2H, bs), 6.42 (1H, s), 6.2 (1H, m), 5.3 (2H, m), 3.8 (2H, m), 2.3 (6H, s), 2.2 (2H, m), 1.5 (2H, m).

IR $\nu_{max}^{cm^{-1}}$ (KBr): 3280, 1780, 1775, 1760, 1660, 1560.

EXAMPLE 12

Preparation of (6R, 7S)-7-[(S) and (R)-2-(2-aminothiazol-4-yl)-2-(3,4-diacetoxybenzamido) acetamido]-1-azabicyclo[4,2,0]-oct-2-en-8-oxo-2-carboxylic acid [another method for preparing the compounds of Examples 6 and 7):

At first, 1.21 g of (6R, 7S)-7-[2-(2-tritylaminothiazol-4-yl)-2-syn-methoxyiminoacetamido]-1-azabicyclo[4,2,0]-oct-2-en-8-oxo-2-carboxylic acid is dissolved in 24 ml of acetic acid, and 2.0 g of zinc powder is added thereto at room temperature with stirring. The mixture is heated to 55°–60° C. with stirring and subjected to reaction for 4 hours. The reaction mixture is filtered and the filtrate is concentrated under reduced pressure. The residue is dissolved in 100 ml of chloroform, and the solution is washed with water and with a saturated aqueous sodium chloride solution and dried with anhydrous sodium sulfate. Then, the solvent is distilled off under reduced pressure. The resulting yellowish powder is dissolved in 20 ml of methylene chloride, and 0.28 ml of triethylamine and 513 mg of 3,4-diacetoxybenzoyl chloride are added thereto. The mixture is stirred at room temperature for one hour. The reaction mixture is concentrated, and 100 ml of methyl acetate and 100 ml of water are added to the residue to obtain a solution. The organic layer is washed with 100 ml of water, and concentrated. The residue is dissolved in 1 ml of chloroform, and the solution is subjected to column chromatography with 50 g of silica gel (Wako gel C-200, made by Wako Junyaku Co.). Elution is carried out with chloroform:methanol=50:1, where fractions each of 10 ml are obtained, whereby 480 mg of the fractions having the R$_f$ value of 0.28 by TLC (silica gel developing solvent chloroform:methanol=5:1) (fraction Nos. 50–62) (compound A) and 510 mg of the fractions having the R$_f$ value of 0.22 (fraction Nos. 67–77) (compound B) are obtained each as yellowish powder.

(1) At first, 450 mg of compound A is dissolved in 20 ml of methanol and 2 ml of water, and the solution is adjusted to pH 1.5 with 1 N hydrochloric acid and heated at 50° C. for one hour. The reaction mixture is concentrated under reduced pressure, and the residue is dissolved in 1 ml of dimethylsulfoxide. The solution is subjected to purification by column chromatography with 50 ml of Diaion HP-10 (eluting solvent methanol:water=2:1), whereby 310 mg of white powder is obtained. The powder is identical with the compound obtained in Example 6 in NMR and IR and is identified to be (6R, 7S)-7-[(S)-2-(2-aminothiazol-4-yl)-2-(3,4-diacetoxybenzamido) acetamido]-1-azabicyclo[4,2,0]-oct-2-en-8-oxo-2-carboxylic acid. Yield: 27.9%.

(2) By treating 470 mg of compound B in the same manner as in the said item 1), 285 mg of white powder is obtained. The powder is identical with the compound obtained in Example 7 in NMR and IR, and is identified to be (6R, 7S)-7-[(R)-2-(2-aminothiazol-4-yl)-2-(3,4-diacetoxybenzamido) acetamido]-1-azabicyclo [4,2,0]-oct-2-en-8-oxo-2-carboxylic acid. Yield: 25.7%.

EXAMPLE 13

Preparation of (6R, 7S)-7-[(S)-2-(2-aminothiazol-4-yl)-2-(3,4-dihydroxybenzamido) acetamido]-1-azabicyclo[4,2,0]-oct-2-en-8-oxo-2-carboxylic acid:

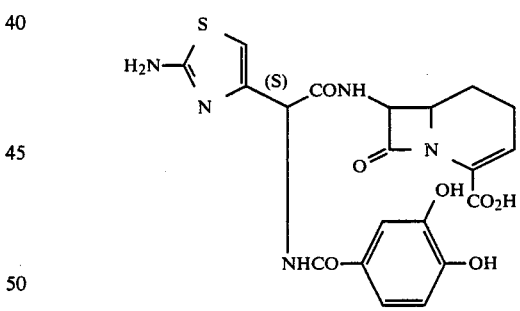

By treating 120 mg of the compound obtained in Example 6 in the same manner as in Example 2, 92 mg of light brown powder is obtained. The powder has the following physical properties and is identified to be the desired compound. Yield: 90.3%.

NMR (DMSO-d$_6$-CD$_3$OD) δ: 7.3 (2H, m), 6.80 (1H, d), 6.52 (1H, s), 6.35 (1H, m), 5.55 (1H, s), 5.33 (1H, d), 3.83 (1H, m), 2.4 (2H, m), 1.8 (2H, m).

EXAMPLE 14

Preparation of 7-[2-(2-aminothiazol-4-yl)-2 (3,4-diacetoxybenzamido) acetamido]-3-acetoxymethyl-3-cephem-4-carboxylic acid:

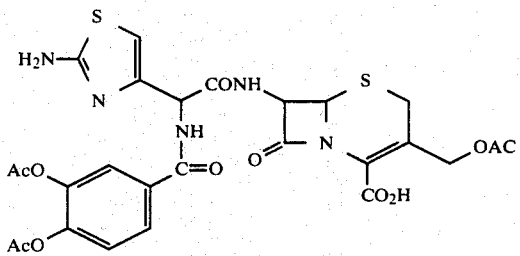

At first, 58 mg (0.136 millimoles) of 7-[2-(2-aminothiazol-4-yl) glycylamido]-3-acetoxymethyl-3-cephem-4carboxylic acid obtained according to the method disclosed in GB No. 2015511A is suspended in 2 ml of tetrahydrofuran. Then, 0.6 ml of N,O-bis(trimethylsilyl) acetamide is added thereto with ice cooling, and the mixture is stirred at the same temperature for 10 minutes and then at room temperature for 30 minutes. A solution of 34.9 mg (0.136 millimoles) of 3,4-diacetoxybenzoyl chloride in 0.5 ml of tetrahydrofuran is added to the former solution, and the mixture is stirred at the same temperature for 30 minutes. Tetrahydrofuran is distilled off under reduced pressure, and the residue is dissolved in a small amount of dimethylsulfoxide. The solution is subjected to column chromatography with Diaion HP-10, and developed with water-methanol. The relevant fractions are concentrated to obtain 42 mg of the desired compound (yield: 48%).

NMR*(DMSO-$d_6$-$D_2O$) δ ppm: 2.05 (3H, s), 2.31 (6H, s), 3.30–3.80 (2H, m), 4.78, 5.03 (2H, ABq, J=12 Hz), 5.06, 5.08 (1H, d, J=5 Hz), 5.63 (1H, s), 5.70, 5.82 (1H, d, J=5 Hz), 6.59 (1H, s), 7.36–7.90 (3H, m).

IR $\nu_{max}^{cm-1}$ (KBr): 3330, 1780, 1760, 1660, 1635, 1530, 1495.

EXAMPLE 15

Preparation of (6R, 7S, 4R)-7-[2-(2-aminothiazol-4-yl)-2-(3,4-diacetoxybenzamido) acetamido]-4-hydroxy-1-azabicyclo [4,2,0]-oct-2-en-8-oxo-2-carboxylic acid:

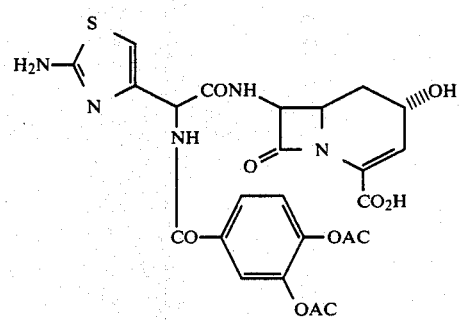

At first, 403 mg of sodium (6R, 7S, 4R)-7-[2-(2-aminothiazol-4-yl)-2-syn-methoxyimino-acetamido]-4-hydroxy-1-azabicyclo[4,2,0]-oct-2-en-8-oxo-2-carboxylate obtained according to the method disclosed in EP No. 0027882A1 is dissolved in 10 ml of acetic acid and 2 ml of water, and 350 mg of zinc powder is added thereto at room temperature. The mixture is stirred for one hour and 30 minutes. The insoluble matters are filtered off, and the filtrate is concentrated under reduced pressure. The residue is dissolved in 10 ml of water, and hydrogen sulfide is bubbled into the solution for 10 minutes. The deposited precipitate is filtered off, and 10 ml of tetrahydrofuran is added to the filtrate. The mixture is adjusted to pH 6.8 with a saturated aqueous sodium bicarbonate solution. Then, a solution of 256 mg of 3,4-diacetoxybenzoyl chloride in 2 ml of tetrahydrofuran is added thereto while keeping pH 6.5–7.0 with a saturated aqueous sodium bicarbonate solution, and the resulting mixture is stirred at room temperature for 30 minutes. Tetrahydrofuran is distilled off from the reaction mixture under reduced pressure, and the mixture is washed with 15 ml of ethyl acetate, adjusted to pH 2.0 with 1 N hydrochloric acid and concentrated under reduced pressure. The residue is dissolved in a small amount of dimethylsulfoxide, and the solution is subjected to purification by column chromatography with 50 ml of Diaion HP-10 (eluting solvent water:methanol = 1:1), whereby 280 mg of white powder is obtained. The powder has the following physical properties and is identified to be the desired compound. Yield: 48.9%.

NMR*(DMSO-$d_6$-$CD_3OD$)δ: 7.8 (2H, m), 7.33 (1H, d), 6.56 (1H, s), 6.33, 6.30 (1H, d), 5.62, 5.58 (1H, s), 5.50, 5.43 (1H, d), 3.9 (1H, m), 2.30 (6H, s), 2.0–1.6 (2H, m).

IR $\nu_{max}^{cm-1}$ (KBr): 3340, 1790, 1785, 1770, 1755, 1660, 1640, 1590, 1525, 1495.

EXAMPLE 16

Preparation of (6R, 7S)-7-[(S)-2-(2-aminothiazol-4-yl)-2-(3,4-diethoxycarbonyloxybenzamido) acetamido]-1-azabicyclo-[4,2,0]-oct-2-en-8-oxo-2-carboxylic acid:

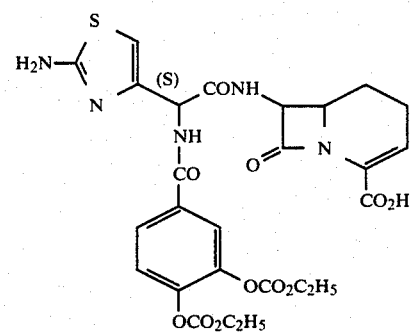

At first, 540 mg of (6R, 7S)-7-[(S)-2-(2-aminothiazol-4-yl)-2-aminoacetamido]-1-azabicyclo [4,2,0]oct-2-en-8-oxo-2-carboxylic acid hydrochloride is dissolved in 15 ml of water and 15 ml of tetrahydrofuran, and the resulting solution is adjusted to pH 7.4 with a saturated aqueous sodium bicarbonate solution. Then, a solution of 450 mg of 3,4-diethoxycarbonyloxybenzoyl chloride in 5 ml of tetrahydrofuran is added thereto at room temperature. The reaction mixture is stirred at room temperature for one hour, and then tetrahydrofuran is distilled off under reduced pressure. Then, 15 ml of water is added to the residue, and the resulting mixture is adjusted to pH 3.0 with 1 N hydrochloric acid, and the deposited white powder is separated by filtration, whereby 720 mg of powder having the following physical properties is obtained. The power is identified to be the desired compound. Yield: 80.6%.

NMR*(DMSO-$d_6$-$CD_3OD$) δ: 7.9 (2H, m), 7.43 (1H, d), 6.55 (1H, s), 6.37 (1H, m), 5.60 (1H, s), 5.37 (1H, d), 4.30 (4H, q), 3.80 (1H, m), 2.4–1.5 (4H, m), 1.37 (6H, s).

IR (KBr) $\nu_{max}^{cm-1}$: 3280, 1780, 1770, 1760, 1660, 1640 1635, 1550, 1540, 1270.

EXAMPLE 17

Preparation of 7-[2-(2-aminothiazol-4-yl)-2-(3,4dihydroxybenzamido) acetamido]-3-[(1-carboxymethyl-5tetrazol) thiomethyl-3-cephem-4-carboxylic acid:

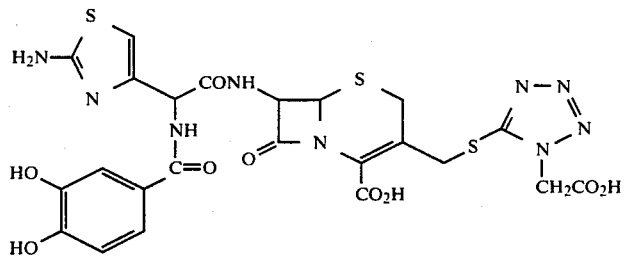

At first, 648 mg of 7-[2-(2-aminothiazol-4-yl)-2-(3,4-diacetoxybenzamido) acetamido]-3-acetoxymethyl-3-cephem-4-carboxylic acid and 224 mg of 5-mercapto-1-carboxymethyltetrazole are dissolved in 12.5 ml of dimethylformamide.

Separately, 555 mg of sodium bicarbonate is dissolved in 25 ml of a 0.1 M sodium phosphate buffer at pH 6.4, and the resulting solution is added dropwise to the first solution with stirring at 70° C. over 40 minutes. After the dropwise addition, the mixture is stirred at the same temperature for 3.5 hours. Then, the mixture is cooled to room temperature, and adjusted to pH 1.0 with concentrated hydrochloric acid. The mixture is charged onto a column of Diaion HP-10 and developed with water-methanol. The fractions eluted with water-methanol from 1:1 to 1:15 are joined together, concentrated to about 5 ml, adjusted to pH 9 with a saturated sodium bicarbonate solution, and again charged onto a column of Diaion HP-10. Fractions eluted with water and water-methanol of 20:1 are joined together, and concentrated to dryness to obtain 176 mg of disodium salt of the desired compound (yield: 25%).

NMR*(D$_2$O) δ ppm: 3.50, 3.56 (2H, each ABq, J=18 Hz), 4.19, 4.20 (2H, each ABq, J=13 Hz), 5.00, 5.01 (2H, each s), 5.05, 5.09 (1H, each d, J=5 Hz), 5.55, 5.56 (1H, each s), 5.61, 5.69 (1H, each d, J=5 Hz), 6.71, 6.76 (1H, each s), 6.88-7.34 (3H, m).

IR (KBr) $\nu_{max}^{cm-1}$: 3350, 1770, 1760, 1640, 1620, 1600, 1525, 1505, 1390.

EXAMPLE 18

Synthesis of 7-[2-(2-aminothiazol-4-yl)-2-(3,4-dihydroxybenzamido) acetamido]-3-(4-carbancylpyridinium)-methyl-3-cephem-4-carboxylate:

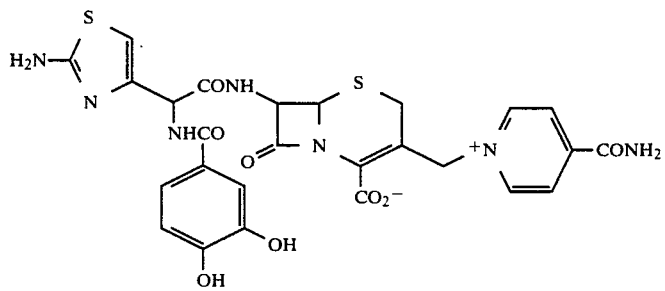

At first, 5 ml of water is added to 2.885 g (5.115 m-moles) of 7-[2-(2-aminothiazol-4-yl)-2-(3,4-dihydroxybenzamido) acetamido-3-cephem-4-carboxylic acid, and the resulting mixture is adjusted to pH 6.5 with a saturated aqueous sodium bicarbonate solution. Then, 2.565 g (20.972 m-moles) of isonicotinamide and 9.585 g of sodium iodide are added to the mixture, and heated to 80° C. with stirring for 1.5 hours. The reaction mixture is cooled to room temperature, and then 10 ml of water is added thereto. The mixture is adjusted to pH 4 with 1 N hydrochloric acid. The deposited insoluble matters are separated by filtration, and the filtrate is subjected to column chromatography with 500 ml of Diaion HP-10. Elution is carried out with 2.5 l of water, water/methanol [=5/1 (v/v)] and water/methanol [=3/2 (v/v)] in this order, and the fractions containing the desired compound are joined together and concentrated under reduced pressure to obtain 4.70 mg of the desired compound (yield: 14.7%).

NMR*(δ ppm in DMSO d$_6$-D$_2$O): 3.10–4.20 (2H, m), 4.90–5.15 (1H, m), 5.20–5.80 (4H, m), 6.50[1H, s), 6.65–7.40 (3H, m), 8.40 (2H, d, J=6.0), 9.44 (2H, d, J=6.0).

EXAMPLE 19

Synthesis of sodium 7-[2-(2-aminothiazol-4-yl)-2-(3,4-dihydroxybenzamido) acetamido]-3-(4-sulfoethylpyridinium)-methyl-3-cephem-4-carboxylate:

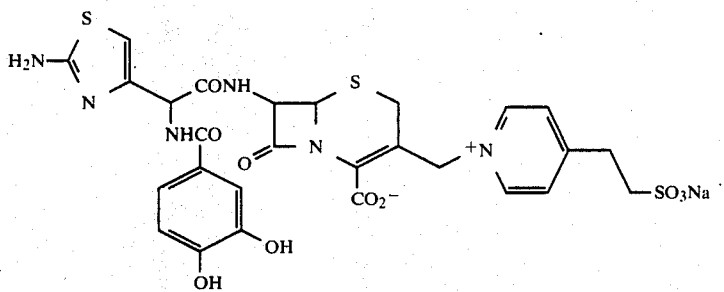

At first, 35 ml of water is added to 3.948 g (7 m-moles) of 7-[2-(2-aminothiazol-4-yl)-2-(3,4-dihydroxybenzamido) acetamido]-3-cephem-4-carboxylic acid and 2.621 g (14 m-moles) of 2-(4-pyridyl) ethanesulfonic acid, and the resulting mixture is adjusted to pH 6.8 with an aqueous 2 N sodium hydroxide solution. Then, 28 g of sodium iodide is added to the resulting solution, and the mixture is heated to 70° C. with stirring for 2 hours. The reaction mixture is cooled to room temperature, and then subjected to column chromatography with 600 ml of Diaion HP-10. After washing with 1.8 l of water, the column is eluted with water/methanol [=8/1 (v/v)], and the fractions containing the desired compound are joined together, and concentrated under reduced pressure to obtain 820 mg of the crude product.

The crude product is dissolved in water, and the solution is again subjected to column chromatography with 200 ml of Diaion HP-10, and the column is washed with 600 ml of water, and then eluted with water/methanol [=20/1 (v/v)]. Fractions containing the desired compound are joined together, and concentrated under reduced pressure to obtain 457 mg of the desired compound (yield: 9.1%).

NMR*($\delta$ ppm in $D_2O$): 3.00–3.70 (2H, m), 3.29 (4H, s), 5.08 (1H, d, J=5.0), 5.01–5.60 (2H, m), 5.52–5.73 (2H, m), 6.66 (1H, s), 6.70–7.40 (3H, m), 7.85 (2H, d, J=6.0), 8.72 (2H, d, J=6.0).

EXAMPLE 20

Method for preparing (S)-2-(3,4-diacetoxybenzamido)-2-(2-chloroacetamido-4-thiazolyl) acetic acid:

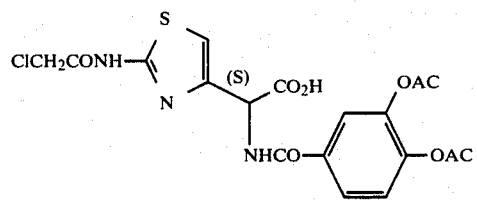

At first, 1 ml of an aqueous 0.2 N sodium bicarbonate solution is added to 50 mg of (S)-2-amino-2-(2-chloroacetamido-4-thiazolyl) acetic acid. The mixture is heated to dissolve the acetic acid and then cooled with ice. Then, a solution of 77 mg of 3,4-diacetoxybenzoic acid chloride in 0.5 ml of acetone is added thereto, and the reaction mixture is adjusted to pH 7.0–7.2 with an aqueous 0.4 N sodium bicarbonate solution.

The mixture is stirred with ice cooling for 30 minutes and at room temperature for 30 minutes, and adjusted approximately to pH 1 with 1 N hydrochloric acid. The mixture is extracted three times with ethyl acetate, and the organic layers are joined together, washed three times with a saturated aqueous sodium chloride solution, and then dried over sodium sulfate. The sodium sulfate is filtered off, and 2 ml of chloroform is added to the oily matters resulting from concentration under reduced pressure. Deposited crystals are separated by filtration, and dried to obtain 55 mg of the desired compound (yield: 58.5%).

NMR ($CDCl_3$-$CD_3OD$) $\delta$: 7.80–7.20 (3H, m), 7.13 (1H, s), 5.83 (1H, s), 4.23 (2H, s), 2.30 (6H, s).

EXAMPLE 21

Antibacterial activities of the present compounds (MIC $\mu$g/ml) by Mueller-Hinton dilution method are shown in the following Table.

| Tested micro-organism | Ex. 1 | Ex. 2 | Ex. 3 | Ex. 4 | Ex. 5-3 | Ex. 6 | Ex. 9 | Ex. 10 | Ex. 11 |
|---|---|---|---|---|---|---|---|---|---|
| a | 6.25 | 12.5 | 3.13 | 1.56 | 0.78 | 12.5 | 12.5 | 12.5 | 50 |
| b | 0.2 | 0.39 | 0.39 | 0.78 | 0.05 | 0.02 | 0.39 | 0.2 | 0.2 |
| c | 0.39 | 0.39 | 0.39 | 0.78 | 0.2 | 0.02 | 0.39 | 0.1 | 0.2 |
| d | 25 | 25 | 1.56 | 1.56 | — | 0.39 | 6.25 | 12.5 | 6.25 |
| e | 0.78 | 0.78 | 0.2 | 0.39 | 0.05 | 0.02 | — | 0.2 | 0.39 |
| f | 0.05 | 0.05 | 0.02 | 0.05 | — | ≦0.01 | — | ≦0.01 | 0.02 |
| g | 0.39 | 0.2 | 0.39 | 0.78 | — | 0.02 | 0.39 | 0.78 | 0.78 |
| h | 0.39 | 0.39 | 1.56 | 1.56 | — | 0.39 | 0.2 | 0.78 | 1.56 |
| i | 0.78 | 1.56 | 0.78 | 1.56 | — | 0.05 | 1.56 | 0.2 | 0.39 |

-continued

| Tested micro-organism | Compound | | | | | | | | |
|---|---|---|---|---|---|---|---|---|---|
| | Ex. 1 | Ex. 2 | Ex. 3 | Ex. 4 | Ex. 5-3 | Ex. 6 | Ex. 9 | Ex. 10 | Ex. 11 |
| j | 3.13 | 6.25 | 3.13 | 3.13 | — | 3.13 | 1.56 | 3.13 | 25 | a: *Staphilococcus aureus* 209P
b: *E. coli* GN2411-5
c: *Klebsiella pneumoniae* 8045
d: *Serratia marcescens* B
e: *Proteus vulgaris* 6897
f: *Proteus rettgeri* 4289
g: *Enterobacter aerogenes* F-1949
h: *Pseudomonas aeruginosa* 145
i: *Pseudomonas putida* F-264
j: *Alcaligenes* F-2518

REFERENCE EXAMPLE 1

Procedure for preparing (6R, 7S)-7-[2-(2-aminothiazol-4-yl)-2-aminoacetamido]-1-azabicyclo[4,2,0]oct-2-en-8-oxo-2-carboxylic acid:

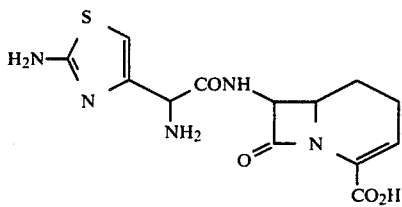

At first, 490 mg of 2-(2-chloroacetamido-4-thiazolyl)-2-chloroacetamidoacetic acid is dissolved in 15 ml of tetrahydrofuran, and the solution is cooled to −10° C. Then, 0.181 ml of N-methylmorpholine and 0.214 ml of isobutyl chloroformate are added thereto, and the mixture is stirred at the same temperature for 30 minutes to prepare a solution of mixed acid anhydride.

Then, 273 mg of (6R, 7S)-7-amino-1-azabicyclo[4,2,0] oct-2-en-8-oxo-2-carboxylic acid is dissolved in 15 ml of water and 15 ml of tetrahydrofuran, and then 0.2 ml of N-methylmorpholine is added thereto. Then, the said solution of mixed acid anhydride is added to the mixture with ice cooling, and the resulting mixture is stirred for 30 minutes, and further subjected to reaction at room temperature for one hour. The reaction mixture is adjusted to pH 2.0 with 1 N hydrochloric acid, and 30 ml of ethyl acetate is added to the solution. The organic layer is separated and washed with a saturated aqueous sodium chloride solution, and the solvent is distilled off under reduced pressure. The residue is dissolved in 20 ml of dimethylacetamide, and 510 mg of thiourea is added to the solution. The mixture is subjected to reaction at room temperature for 18 hours. Then, 50 ml of ethyl ether is added to the reaction mixture, and the deposited precipitate is separated by filtration, and 10 ml of water is added thereto. The mixture is adjusted to pH 2 with 1 N hydrochloric acid for dissolution. The resulting aqueous solution is purified by column chromatography with 100 ml of Diaion HP-10 (eluting solvent water:methanol=5:1), whereby 312 mg of hydrochloride of the desired compound is obtained. Yield: 59.3%.

NMR*(D$_2$O) δ: 7.02 (1H, s), 6.53 (1H, m), 5.52, 5.36 (1H, d), 5.23 (1H, s), 3.9 (1H, m), 2.3 (2H, m), 1.9–1.2 (2H, m).

IR $\nu_{max}^{cm^{-1}}$ (KBr): 3200, 1775, 1760, 1700, 1650, 1635, 1530.

REFERENCE EXAMPLE 2

Preparation of (6R, 7S)-7-[2-(2-aminothiazol-4-yl)-2-aminoacetamido]-1-azabicyclo [4,2,0]-oct-2-en-8-oxo-2-carboxylic acid (another method):

At first, 10 g of (6R, 7S)-7-[2-(2-aminothiazol-4-yl)-2-syn-methoxyiminoacetamido]-1-azabicyclo [4,2,0]-oct-2-en-8-oxo-2-carboxylic acid is dissolved in 185 ml of acetic acid, and 7.0 g of zinc powder is added thereto by portions with stirring. The mixture is subjected to reaction at room temperature for 2 hours. The reaction mixture is filtered, the filtrate is concentrated under reduced pressure, and 150 ml of water is added to the residue. The mixture is again concentrated under reduced pressure. The residue is dissolved in 50 ml of water, and the mixture is adjusted to pH 2.0 with concentrated hydrochloric acid and purified by column chromatography with 1,000 ml of Diaion HP-10 (eluting solvent water:methanol=5:1), whereby 8.1 g of white powder is obtained. The white powder is identical with the compound obtained in Reference Example 1 in R$_f$value of TLC, NMR and IR, and is identified to be the desired compound. Yield: 76.7%.

REFERENCE EXAMPLE 3

Preparation of (6R, 7S)-7-[(R)-2-(2-aminothiazol-4-yl)-2-aminoacetamido]-1-azabicyclo [4,2,0] oct-2-en-8-oxo-2-carboxylic acid:

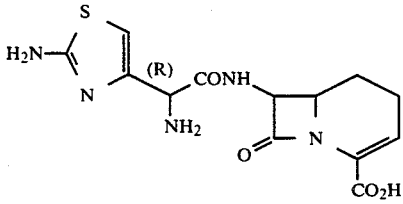

According to the same procedures as in Reference Example 1 except that (R)-2-(2-chloroacetamido-4-thiazolyl)-2-chloroacetamidoacetic acid [angle of rotation $[\alpha]_D^{23} = -150.2$ (c=1, 0.1 N NaOH)] is used in place of 2-(2-chloroacetamido-4-thiazolyl)-2-chloroacetamidoacetic acid as used in Reference Example 1, 360 mg of white powder is obtained. The white powder is identified to be the hydrochloride of the desired compound. Yield: 68.4%.

NMR (D$_2$O) δ: 7.01 (1H, s), 6.52 (1H, m), 5.51 (1H, d), 5.20 (1H, s), 3.9 (1H, m), 2.3(2H, m), 1.8–1.2 (2H, m).

REFERENCE EXAMPLE 4

Preparation of (6R, 7S)-7-[(S)-2-(2-aminothiazol-4-yl)-2-aminoacetamido]-1-azabicyclo [4,2,0] oct-2-en-8-oxo-2-carboxylic acid:

According to the same procedure as in Reference Example 1 except that (S)-2-(2-chloroacetamido-4-thiazolyl)-2-chloroacetamidoacetic acid [angle of rotation $[\alpha]_D^{25} = +145.8$ (c=1, 0.1 N NaOH)] is used in place of 2-(2-chloroacetamido-4-thiazolyl)-2-chloroacetamidoacetic acid as used in Reference Example 1, 298 mg of white powder is obtained. The white powder is identified to be the hydrochloride of the desired compound. Yield: 56.6%.

NMR (D$_2$O)$\delta$: 7.02 (1H, s), 6.52 (1H, m), 5.36 (1H, d), 5.21 (1H, s), 3.9 (1H, m), 2.3 (2H, m), 1.8–1.2 (2H, m).

What is claimed is:

1. A $\beta$-lactam compund of the formula:

wherein
Y is a hydroxyl group, a lower alkanoyloxy group or a lower alkoxycarbonyloxy group;
W is a group represented by CH$_2$, NH, $$\text{NHC, N(CH}_3\text{)C, CH=CH, CH}_2\text{NHC or CH}_2\text{C;}$$
$$\text{\quad\ \ \ \|\quad\quad\quad\ \ \|\quad\quad\quad\quad\quad\quad\quad\quad\quad\ \ \|\quad\quad\quad\ \|}$$
$$\text{\quad\ \ \ O\quad\quad\quad\ \ O\quad\quad\quad\quad\quad\quad\quad\quad\quad O\quad\quad\quad O}$$

A is a phenyl group, a naphthyl group, or a chromonyl group, respectively substituted by (Y)$_n$;
R$_1$ is a hydrogen atom, a hydroxyl group, a methoxy group or a lower alkyl group;
R$_2$ is a hydrogen atom, a halogen atom, a methoxy group or a group represented by CH$_2$R$_2'$ wherein R$_2'$ is a hydrogen atom, an azido group, a lower alkanoyloxy group, a carbamoyloxy group, a pyridinium group, a substituted pyridinium group wherein the substituent is —(CH$_2$)$_p$—R$_A$ wherein R$_A$ is a carbamoyl group, carboxyl group, cyano group or lower alkoxycarbonyl group having 2 to 5 carbon atoms, and p is 0, 1, 2 or 3; or —R$_B$—SO$_3$—R$_C$ wherein R$_B$ is a lower alkylene group having 1 to 3 carbon atoms, and R$_C$ has the same meaning as R$_3$, or
a substituted or unsubstituted heterocyclic thio group wherein the heterocyclic group is a tetrazolyl group, thiadiazolyl group, triazolyl group, triazinyl group or thiazolyl group and wherein the substituent is a lower alkyl group having 1 to 5 carbon atoms, hydroxyl group, oxo group, amino group, nitro group, (CH$_2$)$_q$CO$_2$H, (CH$_2$)$_q$CO$_2$—(alkyl group having 1–4 carbon atoms), (CH$_2$)$_q$SO$_3$H, (CH$_2$)$_q$—N (alkyl group having 1-4 carbon atoms)$_2$, and q represents an integer of 1 to 3;
R$_3$ is a hydrogen atom, an alkali metal, an alkaline earth metal, an ammonium group of a basic amino acid or an ester residue represented by the formula:

$$-\text{CH}-\text{OC}-\text{R}_7$$
$$\ \ \ \ |\quad\ \ \ \ \|$$
$$\ \ \ \text{R}_6\quad\ \ \text{O}$$

wherein R$_6$ represents a hydrogen atom or a lower alkyl group having 1 to 6 carbon atoms, and R$_7$ represents a lower alkyl group having 1 to 6 carbon atoms, or a phenyl group, or the formula R$_4$ and R$_5$ each are hydrogen atom, a lower alkyl group or a cycloalkylidene group with a carbon atom combined therewith; l is 0 or an integer of 1, 2 or 3; m is 0 or 1; and n is an integer of 1, 2, 3, 4 or 5.

2. A $\beta$-lactam compound according to claim 1 where l is 0.

3. A $\beta$-lactam compound according to claim 2 wherein R$_1$ is a hydrogen atom or a hydroxyl group, R$_2$ is a hydrogen atom, A is a phenyl or chromonyl group respectively substituted by (Y)$_n$, m is 0 or 1, and when m is 1, $$\text{W is NHC, CH=CH, or CH}_2\text{NHC.}$$
$$\quad\quad\ \ \|\quad\quad\quad\quad\quad\quad\quad\quad\ \ \|$$
$$\quad\quad\ \ O\quad\quad\quad\quad\quad\quad\quad\quad\ O$$

4. An antimicrobial pharmaceutical composition which comprises an effective antimicrobial amount of a composition of matter according to claim 1 and at least one member of the group consisting of pharmaceutically acceptable diluents, carriers and adjuvants.

5. A method for treating bacterial infection in mammals which comprises administering the pharmaceutical composition of claim 1 at a dosage level of between 5 and 350 mg of active ingredient per kilogram of body weight.

* * * * *

UNITED STATES PATENT AND TRADEMARK OFFICE
CERTIFICATE OF CORRECTION

PATENT NO. : 4,694,001

DATED : September 15, 1987

INVENTOR(S) : TADASHI HIRATA, ET AL.

It is certified that error appears in the above-identified patent and that said Letters Patent is hereby corrected as shown below:

Column 8, formula I" should read:

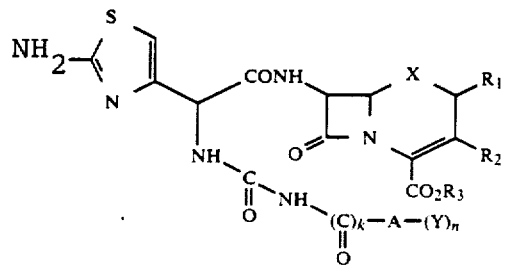

(I")

Column 9, line 66, "LO(VIII)" should read --L-(VIII)--.

Column 13, line 40, "Grae-negative" should read
--Gram-negative--.

Column 15, line 55, "-lazabibyclo" should read
-- -1-azabicyclo--.

UNITED STATES PATENT AND TRADEMARK OFFICE
CERTIFICATE OF CORRECTION

PATENT NO. : 4,694,001
DATED : September 15, 1987
INVENTOR(S) : TADASHI HIRATA, ET AL.

It is certified that error appears in the above-identified patent and that said Letters Patent is hereby corrected as shown below:

Column 16, line 4, delete "*The same shall apply hereinafter."

Column 17, line 32, "[4,2,0]" should read --[4,2,0]- --.

Column 18, in the last line of the Table, after "2.2", add --(2H,m), 1.6(2H,m)--.

Column 19, line 32, "aminothiazol4-" should read --aminothiazol-4- --.

Column 19, line 53, "-2carboxylic" should read -- -2-carboxylic--.

Column 20, line 50, "lazabicyclo" should read --1-azabicyclo--.

Column 22, line 45, "lazabicyclo" should read --1-azabicyclo--.

Column 24, line 65, "-2 (3,4-" should read -- -2-(3,4- --.

Column 25, line 15, "4carboxylic" should read --4-carboxylic--.

Column 27, line 3, "(3,4dihy-" should read --(3,4-dihy- --.

Column 28, line 4, "(4-carbancylpyridinium)-" should read --(4-carbamoylpyridinium)- --.

UNITED STATES PATENT AND TRADEMARK OFFICE
CERTIFICATE OF CORRECTION

PATENT NO. : 4,694,001
DATED : September 15, 1987
INVENTOR(S) : TADASHI HIRATA, ET AL.

It is certified that error appears in the above-identified patent and that said Letters Patent is hereby corrected as shown below:

Column 33, line 28, "compund" should read --compound--.

Signed and Sealed this

Twenty-third Day of February, 1988

Attest:

DONALD J. QUIGG

*Attesting Officer*   *Commissioner of Patents and Trademarks*